US00PP23144P2

(12) United States Plant Patent
Danziger

(10) Patent No.: US PP23,144 P2
(45) Date of Patent: Oct. 23, 2012

(54) ***DIASCIA* PLANT NAMED 'DGENT31'**

(50) Latin Name: *Diascia barerae*
Varietal Denomination: DGENT31

(75) Inventor: Gavriel Danziger, Moshav Mishmar Hashiva (IL)

(73) Assignee: Danziger 'DAN' Flower Farm

( * ) Notice: Subject to any disclaimer, the term of this patent is extended or adjusted under 35 U.S.C. 154(b) by 0 days.

(21) Appl. No.: 13/066,971

(22) Filed: Apr. 29, 2011

(51) Int. Cl.
*A01H 5/00* (2006.01)

(52) U.S. Cl. ..... Plt./425

(58) Field of Classification Search ..... Plt./425
See application file for complete search history.

*Primary Examiner* — Annette Para
(74) *Attorney, Agent, or Firm* — Cassandra Bright

(57) ABSTRACT

A new and distinct *Diascia* cultivar named 'DGENT31' is disclosed, characterized by large pink flowers. The new variety has a good temperature tolerance range for *Diascia*. The new variety is a *Diascia*, normally produced as an outdoor garden or container plant.

2 Drawing Sheets

Latin name of the genus and species: *Diascia barerae.*
Variety denomination: 'DGENT31'.

BACKGROUND OF THE INVENTION

The new *Diascia* cultivar is a product of a planned breeding program conducted by the inventor, Gavriel Danziger, in Moshav Mishmar Hashiva, Israel. The objective of the breeding program was to produce new *Diascia* varieties for ornamental commercial applications. The cross resulting in this new variety was made during September 2008.

The seed parent is the unpatented, proprietary seedling variety referred to as *Diascia barerae* 'Di-7-1049' The pollen parent is unknown, as the crossing resulting in 'DGENT31' was an open pollination, with unidentifiable pollen parents. The new variety was discovered in May 2009 by the inventor in a group of seedlings resulting from the 2008 crossing, in a research greenhouse in Moshav Mishmar Hashiva, Israel.

Asexual reproduction of the new cultivar 'DGENT31' by vegetative cuttings was first performed at a research greenhouse in Moshav Mishmar Hashiva, Israel in June 2009 and has shown that the unique features of this cultivar are stable and reproduced true to type in successive generations.

SUMMARY OF THE INVENTION

The cultivar 'DGENT31' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGENT31' These characteristics in combination distinguish 'DGENT31' as a new and distinct *Diascia* cultivar:

1. Large flowers
2. Good temperature tolerance for a *Diascia* plant

Plants of the new cultivar 'DGENT31' are similar to plants of the seed parent, *Diascia barerae* 'DI-7-1049' in most horticultural characteristics, however, plants of the new cultivar 'DGENT31' produce darker pink flowers than the seed parent variety. Additionally, plants of the new variety produce more branches per plant than the seed parent.

COMMERCIAL COMPARISON

Plants of the new cultivar 'DGENT31' are comparable to the variety *Diascia* 'Whisper Pumpkin', unpatented. The two *Diascia* varieties are similar in most horticultural characteristics however, the new variety 'DGENT31' differs in having different color flowers, a longer internode, and larger foliage. Additionally, 'DGENT31' produces large flowers, whereas 'Whisper Pumpkin' produces small flowers.

Plants of the new cultivar 'DGENT31' can also be compared to the commercial variety *Diascia* 'DALA ABLOS' U.S. Plant Pat. No. 20,934. These varieties are similar in most horticultural characteristics, however 'DGENT31' produces larger flowers, and an overall larger size plant.

BRIEF DESCRIPTION OF THE PHOTOGRAPHS

Figure 1:
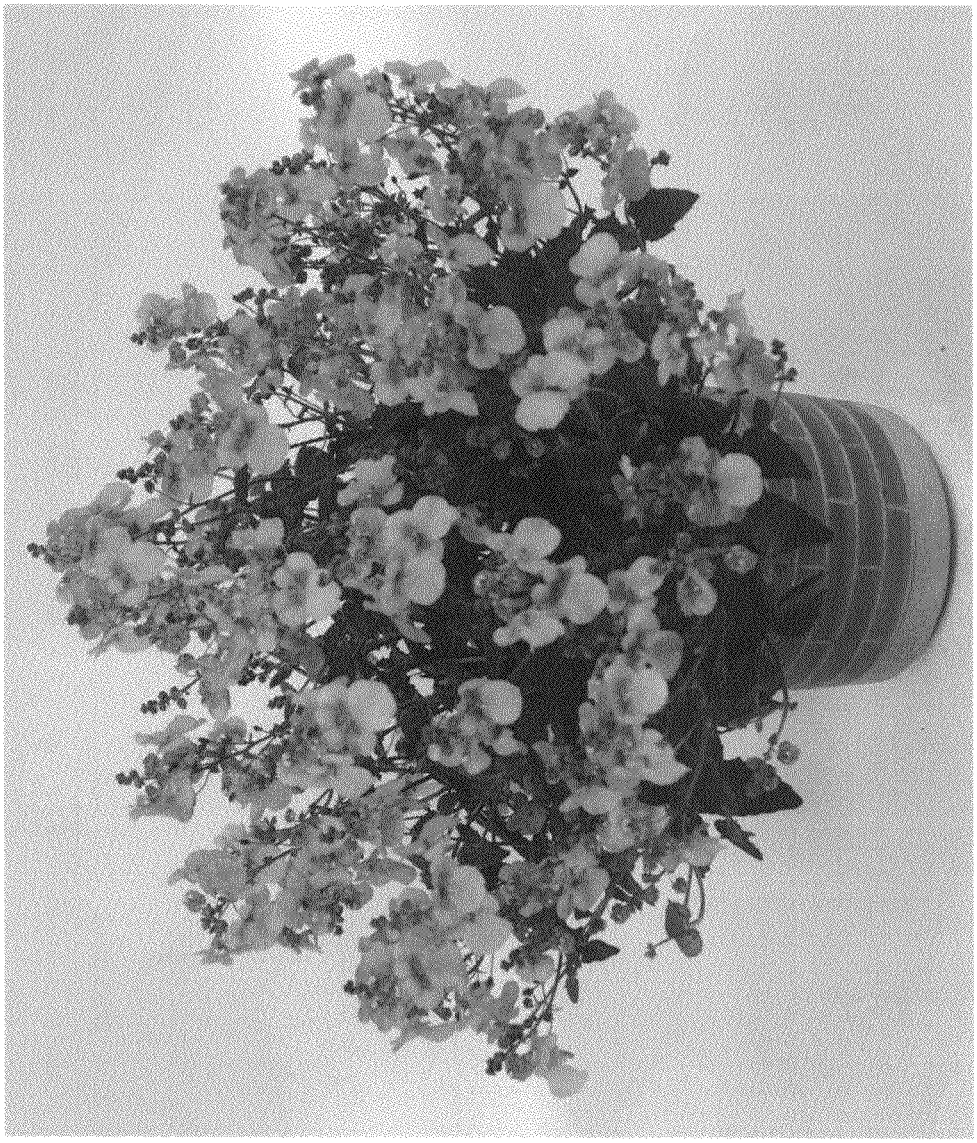

The accompanying photograph in FIG. 1 illustrates in full color a typical plant of 'DGENT31' grown in a greenhouse, in a 13 cm basket. Age of the plant photographed is approximately 3 months from a rooted cutting.

Figure 2:
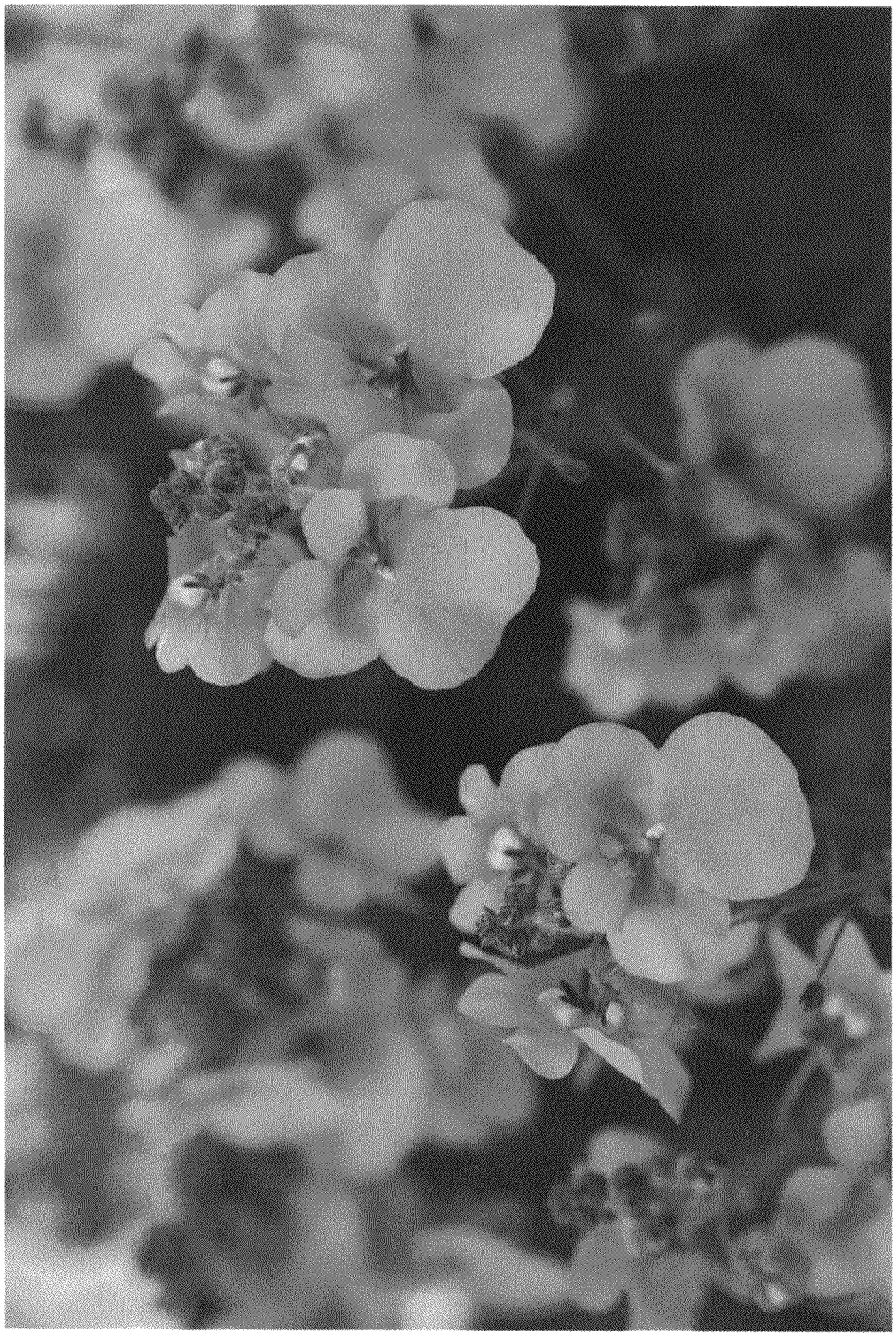

FIG. 2 illustrates in full color a close up of a typical bloom of 'DGENT31'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGENT31' plants grown in a greenhouse, and moved outdoors during Spring in Moshav Mishmar Hashiva, Israel. The growing temperature ranged from 18° C. to 28° C. during the day and from 8° C. to 15° C. during the night. General light conditions are bright, normal sunlight. Measurements and numerical values represent averages of typical plant types. Plants are approximately 70 days old from a rooted cutting.
Botanical classification: *Diascia barerae* 'DGENT31'.

PROPAGATION

Time to initiate roots: About to 8 to 14 days at approximately 20° C.
Root description: Fine, fibrous.

PLANT

Age of plant described: Approximately 70 days from a rooted cutting.
Growth habit: Semi-upright.
Height: Approximately 19 cm.
Plant spread: Approximately 30 cm.
Growth rate: Moderate.
Branching characteristics: Moderate to well branched.
Length of lateral branches: Approximately 2 cm.
Diameter of lateral branches: Approximately 0.3 cm.
Texture of lateral branches: Smooth.
Internode length: Average 4 cm.
Strength of stem: Strong.
Color of lateral branches: Near RHS Green 138-A.
Aspect/angle of branches: 45°.
Number of leaves per lateral branch: Approximately 20.

FOLIAGE

Leaf:
*Arrangement*.—Single and opposite.
*Average length*.—Approximately 3 cm.
*Average width*.—Approximately 2.7 cm.
*Shape of blade*.—Deltoid.
*Apex*.—Obtuse.
*Base*.—Cordate.
*Attachment*.—Stalked.
*Margin*.—Sinuate.
*Texture of top surface*.—Smooth.
*Texture of bottom surface*.—Smooth.
*Appearance top surface*.—Matte.
*Appearance bottom surface*.—Matte.
*Leaf internode length*.—Approximately 4 cm.
*Color*.—Young foliage upper side: Near RHS green 137-C. Young foliage under side: Near RHS yellow green 147-C. Mature foliage upper side: Near RHS green 137-A. Mature foliage under side: Near RHS yellow green 147-C.
*Venation*.—Type: Pinnate. Venation color upper side: Near RHS yellow green 147-B. Venation color under side: Near RHS yellow green 146-C.
*Petiole*.—Length: Average 0.5 cm. Diameter: Average 0.3 cm. Pubescence: None.
*Color*.—Near RHS yellow green 144-B.

FLOWER

Natural flowering season: Spring. Autumn, Winter.
Days to flowering from rooted cutting: 25 to 28.
Flower longevity on plant: 5 days.
Persistent or self-cleaning: Self-Cleaning.
Fragrance: None.
Inflorescence arrangement:
*Inflorescence heigh*.—6.5 cm.
*Inflorescence width*.—4.5 cm.
*Quantity of flowers per inflorescence*.—8.
Individual flower form: Single, zygomorphic, salver-shaped.
Flower:
*Diameter of entire flower*.—Approximately 3.3 cm.
*Length of flower*.—Approximately 3.2 cm.
Bud:
*Bud shape*.—Oblate.
*Bud length*.—Approximately 0.3 cm.
*Bud diameter*.—Approximately 0.3 cm.
*Bud color*.—Near RHS Yellow-Green 154-C.
*Opening rate, from bud to fully open*.—5 Days.
Petals:
*Quantity*.—5.
*Arrangement*.—The two small upper petals nearly entirely fused, two lateral lobes and a broad lower lobe; two short spurs emerge at the underside, formed by the lower ends of lateral and lower petals.
*Length*.—3.0 cm.
*Width*.—2.3 cm.
*Shape*.—Rounded.
*Apex*.—Cordate.
*Base*.—Truncate.
*Margin*.—Entire.
*Texture, upper and lower surfaces*.—Smooth.
*Appearance*.—Matte.
*Color*.—When opening, upper surface: Near RHS Red-Purple 65-B. When opening, lower surface: Near RHS Red-Purple 65-B. Fully opened, upper surface: Near RHS Red-Purple 65-A. Fully opened, lower surface: Near RHS Red-Purple 65-A. Fading, upper surface: Near RHS Purple 75-B. Fading, lower surface: Near RHS Purple 75-B.
Peduncle:
*Peduncle length*.—Approximately 5.0 cm.
*Peduncle diameter*.—Approximately 0.3 cm.
*Angle*.—Approximately 0 deg from center of whorl.
*Color*.—Near RHS Yellow-Green 146-A.
*Peduncle texture*.—Smooth.
Pedicel:
*Pedicel length*.—Approximately 1.7 cm.
*Pedicel diameter*.—Approximately 0.1 cm.
*Angle*.—Approximately 45 deg from center of whorl.
*Color*.—Near RHS Yellow-Green 144-A.
*Pedicel texture*.—Finely pubescent.

REPRODUCTIVE ORGANS

Androecium:
*Stamens*.—4.
*Anther shape*.—Bi lobed.
*Anther length*.—Approximately 0.2 cm.
*Anther color*.—Near RHS red-purple N74-B.
*Pollen quantity*.—Abundant.
*Pollen color*.—Near RHS Yellow 3-A.
Gynoecium:
*Pistil number*.—1.
*Pistil shape*.—Cylindrical.
*Pistil length*.—Approx. 0.4 cm.
*Style length*.—Approx. 0.1 cm.
*Style color*.—Near RHS yellow green 145-D.
*Stigma shape*.—Rounded.
*Stigma color*.—Near RHS yellow green 151-B.

*Ovary diameter.*—1 mm.

*Ovary color*.—Near RHS green group 145-A.

OTHER CHARACTERISTICS

Fruit:

*Shape*.—Piriform.

*Color*.—Near RHS green-yellow 146-B.

*Size*.—Length — 1 cm. Width — 0.5 cm.

Seed: Not observed.

Disease/pest resistance: Neither resistance nor susceptibility to pathogens and pests common to *Diascia* have been observed.

Temperature tolerance: The new variety exhibits a good temperature tolerance range for *Diascia*. Good tolerance for temperatures between −1 to 35° C.

What is claimed is:

1. A new and distinct cultivar of *Diascia* plant named 'DGENT31' as herein illustrated and described.

* * * * *